(12) United States Patent
Le Visage et al.

(10) Patent No.: US 9,028,857 B2
(45) Date of Patent: May 12, 2015

(54) METHOD FOR PREPARING POROUS SCAFFOLD FOR TISSUE ENGINEERING

(75) Inventors: Catherine Le Visage, Paris (FR); Didier Letourneur, Chatenay Malabry (FR); Frederic Chaubet, Eaubonne (FR); Aude Autissier, Aubigny sur Nere (FR)

(73) Assignees: INSERM (Institut National de la Sante et de la Recherche Medicale), Paris (FR); Universite Paris 7—Denis Diderot, Paris Cedex (FR)

( * ) Notice: Subject to any disclaimer, the term of this patent is extended or adjusted under 35 U.S.C. 154(b) by 423 days.

(21) Appl. No.: 12/681,676

(22) PCT Filed: Oct. 10, 2008

(86) PCT No.: PCT/EP2008/063672
§ 371 (c)(1),
(2), (4) Date: Apr. 5, 2010

(87) PCT Pub. No.: WO2009/047347
PCT Pub. Date: Apr. 16, 2009

(65) Prior Publication Data
US 2010/0221301 A1    Sep. 2, 2010

(30) Foreign Application Priority Data
Oct. 11, 2007    (EP) ..................................... 07301451

(51) Int. Cl.
| | |
|---|---|
| A61F 13/00 | (2006.01) |
| C07H 1/00 | (2006.01) |
| C08B 37/02 | (2006.01) |
| A61L 27/20 | (2006.01) |
| A61L 27/38 | (2006.01) |
| A61L 27/50 | (2006.01) |
| A61L 27/52 | (2006.01) |
| A61L 27/56 | (2006.01) |
| C12N 5/00 | (2006.01) |
| C08B 37/00 | (2006.01) |
| C08B 37/08 | (2006.01) |
| C08H 1/06 | (2006.01) |
| C08J 9/28 | (2006.01) |

(52) U.S. Cl.
CPC ............ *A61L 27/20* (2013.01); *A61L 27/3804* (2013.01); *A61L 27/3847* (2013.01); *A61L 27/3852* (2013.01); *A61L 27/507* (2013.01); *A61L 27/52* (2013.01); *A61L 27/56* (2013.01); *C12N 5/0068* (2013.01); C12N 2533/70 (2013.01); *C08B 37/0018* (2013.01); *C08B 37/0021* (2013.01); *C08B 37/003* (2013.01); *C08B 37/0039* (2013.01); *C08B 37/0054* (2013.01); *C08B 37/0063* (2013.01); *C08B 37/0072* (2013.01); *C08B 37/0075* (2013.01); *C08B 37/0084* (2013.01); *C08H 1/06* (2013.01); *C08J 9/28* (2013.01); *C08J 2201/026* (2013.01); *C08J 2201/0484* (2013.01); *C08J 2205/04* (2013.01); *C08J 2207/10* (2013.01); *C08J 2305/00* (2013.01); *C08J 2305/02* (2013.01); *C08J 2305/08* (2013.01); *C08J 2305/12* (2013.01)

(58) Field of Classification Search
CPC . A61L 27/20; A61L 27/3804; A61L 27/3847; C08B 37/0018
USPC ................ 424/422; 435/178; 536/112, 123.1
See application file for complete search history.

(56) References Cited

U.S. PATENT DOCUMENTS

| | | | | |
|---|---|---|---|---|
| 5,840,777 A | * | 11/1998 | Eagles et al. ..................... | 521/82 |
| 2002/0155067 A1 | | 10/2002 | MacGregor | |
| 2002/0187182 A1 | | 12/2002 | Kramer et al. | |
| 2003/0012805 A1 | * | 1/2003 | Chen et al. ..................... | 424/423 |
| 2004/0063206 A1 | | 4/2004 | Rowley et al. | |
| 2013/0224277 A1 | * | 8/2013 | Amedee et al. ............... | 424/423 |

FOREIGN PATENT DOCUMENTS

| | | |
|---|---|---|
| EP | 1166987 | 1/2002 |
| WO | 00/35372 | 6/2000 |
| WO | 03/007786 | 1/2003 |
| WO | 2006/095154 | 9/2006 |
| WO | 2007/056418 | 5/2007 |

OTHER PUBLICATIONS

Cavalcanti et al, Synthesis and characterization of phosphated crosslinked chondroitin sulfate: Potential ingredient for specific drug delivery, Acta Tarm. Bonaerense 24 (2): 234-238 (2005).*
International Search Report and Written Opinion in PCT/EP08/63672, dated Dec. 5, 2008.

* cited by examiner

*Primary Examiner* — Mina Haghighatian
(74) *Attorney, Agent, or Firm* — McAndrews, Held & Malloy Ltd.

(57) ABSTRACT

The present invention relates to a method for preparing a porous scaffold for tissue engineering. It is another object of the present invention to provide a porous scaffold obtainable by the method as above described, and its use for tissue engineering, cell culture and cell delivery. The method of the invention comprise the steps consisting of a) preparing an alkaline aqueous solution comprising an amount of at least one polysaccharide and one cross-linking agent b) freezing the aqueous solution of step a) c) sublimating the frozen solution of step b). characterized in that step b) is performed before the cross-linking of the polysaccharide occurs in the solution of step a).

7 Claims, 6 Drawing Sheets

METHOD FOR PREPARING POROUS SCAFFOLD FOR TISSUE ENGINEERING

Figure 1:
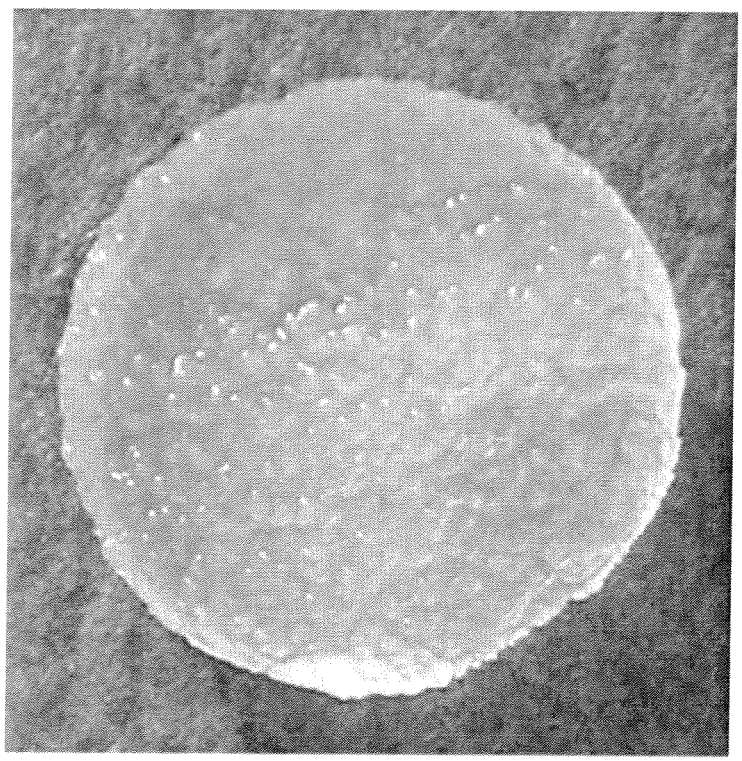

The present application is filed pursuant to 35 U.S.C. 371 as a U.S. National Phase application of International Patent Application No. PCT/EP08/63672, which was filed Oct. 10, 2008, claiming the benefit of priority to European Patent Application No. 07301451.6, which was filed on Oct. 11, 2007. The entire text of the aforementioned applications is incorporated herein by reference in its entirety.

FIELD OF THE INVENTION

The present invention relates to a method for preparing a porous scaffold for tissue engineering. It is another object of the present invention to provide a porous scaffold obtainable by the method as above described, and its use for tissue engineering, cell culture and cell delivery.

BACKGROUND OF THE INVENTION

Tissue engineering is generally defined as the creation of tissue or organ equivalents by seeding of cells onto or into a scaffold suitable for implantation. The scaffolds must be biocompatible and cells must be able to attach and proliferate on the scaffolds in order for them to form tissue or organ equivalents. These scaffolds may therefore be considered as substrates for cell growth either in vitro or in vivo.

The attributes of an ideal biocompatible scaffold would include the ability to support cell growth either in vitro or in vivo, the ability to support the growth of a wide variety of cell types or lineages, the ability to be endowed with varying degrees of flexibility or rigidity required, the ability to have varying degrees of biodegradability, the ability to be introduced into the intended site in vivo without provoking secondary damage, and the ability to serve as a vehicle or reservoir for delivery of drugs, cells and/or bioactive substances to the desired site of action.

A number of different scaffold materials have been utilized, for guided tissue regeneration and/or as biocompatible surfaces. Biodegradable polymeric materials are preferred in many cases since the scaffold degrades over time and eventually the cell-scaffold structure is replaced entirely by the cells. Among the many candidates that may serve as useful scaffolds claimed to support tissue growth or regeneration, are included gels, foams, sheets, and numerous porous particulate structures of different forms and shapes.

Among the manifold natural polymers which have been disclosed to be useful for tissue engineering or culture, one can enumerate various constituents of the extracellular matrix including fibronectin, various types of collagen, and laminin, as well as keratin, fibrin and fibrinogen, hyaluronic acid, heparin sulfate, chondroitin sulfate and others.

Other common polymers that were used include poly(lactide-co-glycolide) (PLG). PLG are hydrolytically degradable polymers that are FDA approved for use in the body and mechanically strong (Thomson R C, Yaszemski M J, Powers J M, Mikos A G. Fabrication of biodegradable polymer scaffolds to engineer trabecular bone. J Biomater Sci Polym Ed. 1995; 7(1):23-38; Wong W H. Mooney D J. Synthesis and properties of biodegradable polymers used as synthetic matrices for tissue engineering. In: Atala A, Mooney D J, editors; Langer R, Vacanti J P, associate editors. Synthetic biodegradable polymer scaffolds. Boston: Birkhäuser: 1997. p. 51-82). However, they are hydrophobic and typically processed under relatively severe conditions, which make factor incorporation and entrapment of viable cells potentially a challenge.

As an alternative, a variety of hydrogels, a class of highly hydrated polymer materials (water content higher than 30% by weight), have been used as scaffold materials. They are composed of hydrophilic polymer chains, which are either synthetic or natural in origin. The structural integrity of hydrogels depends on cross-links formed between polymer chains via various chemical bonds and physical interactions. Hydrogels used in these applications are typically degradable, can be processed under relatively mild conditions, have mechanical and structural properties similar to many tissues and the extracellular matrix, and can be delivered in a minimally invasive manner (Lee K Y, Mooney D J. Hydrogels for tissue engineering. Chem Rev. 2001 July; 101(7):1869-79). Various polymers have therefore been used to process hydrogels. For example, those polymers include collagen, gelatin, hyaluronic acid (HA), and chitosan.

Use of natural polysaccharides represents also a promising alternative for making scaffolds based on hydrogels, because they are non antigenic and non immunogenic, and some of them present antithrombotic effects and interactions with vascular growth factors. Furthermore, due to their plasticity properties, those polysaccharides based hydrogels may be shaped in various forms to allow the design of therapeutic implant or graft biomaterials.

For example, Chaouat et al. (Chaouat M, Le Visage C, Autissier A, Chaubet F, Letourneur D. The evaluation of a small-diameter polysaccharide-based arterial graft in rats. Biomaterials. 2006 November; 27(32):5546-53. Epub 2006 Jul. 20) designed a novel polysaccharide based scaffold prepared by using a mixture of pullulan and dextran. Chemical cross-linking of polysaccharides was carried out using the cross-linking agent trisodium trimetaphosphate (STMP). Thereafter, the effectiveness of an arterial material prepared with this scaffold was demonstrated in vivo.

However, despite the advantageous of using polysaccharides for preparing scaffolds as described in Chaouat et al. (2006), the default of porosity of the resulted scaffold remains a drawback to envisage an effective use for therapeutic purposes. Actually, porosity is an essential feature to allow the proliferation, integration and differentiation of the cells inside the scaffold, so that the material can be used as a cell reservoir to reconstruct in vivo the tissue or organ.

Therefore there is still an existing need in the art to develop a method for preparing porous scaffold matrices that can be used for therapeutic purposes.

SUMMARY OF THE INVENTION

Therefore, it is an object of the present invention to provide a method for preparing a porous scaffold which comprises the steps consisting of
  a) preparing an alkaline aqueous solution comprising an amount of at least one polysaccharide and one cross-linking agent
  b) freezing the aqueous solution of step a)
  c) sublimating the frozen solution of step b).
  characterized in that step b) is performed before the cross-linking of the polysaccharide occurs in the solution of step a).

According to the invention, the term "step b) is performed before the cross-linking of the polysaccharide occurs in the solution of step a)" means that the cross-linking of the polysaccharide occurs during the sublimation step (step c)).

It is another object of the present invention to provide a porous scaffold obtainable by the method as above described.

It is still further an object of the present invention to provide the use of porous scaffold of the invention for tissue engineering.

DETAILED DESCRIPTION OF THE INVENTION

Definitions

The term "polysaccharide", as used herein, refers to a molecule comprising two or more monosaccharide units.

The term "alkaline solution", as used herein, refers to a solution having a pH superior to 7.

The term "aqueous solution", as used herein, refers to a solution in which the solvent is water.

The term "cross-linking" refers to the linking of one polymer chain to another one with covalent bonds.

As used herein, a "scaffold" is defined as a semi-solid system comprising a three-dimensional network of one or more species of polysaccharide chains. Depending on the properties of the polysaccharide (or polysaccharides) used, as well as on the nature and density of the network, such structures in equilibrium can contain various amounts of water.

The term "cross-linking agent" includes any agent able to introduce cross-links between the chains of the polysaccharides of the invention.

The term "biodegradable", as used herein, refers to materials that degrade in vivo to non-toxic compounds, which can be excreted or further metabolized.

The term "sublimation" refers to the physical phase transition from a solid state directly to a vapor state. More specifically, sublimation is a process in which a substance goes from a solid to a gas without going through a liquid phase. Sublimation of a solution may be obtained through the freeze-drying process.

The term "freeze-drying" is the term for the drying of a deep-frozen material under high vacuum by freezing out the solvent (ie. water) and then evaporating it in the frozen state.

Porous Scaffolds and Method for Preparing Thereof

A first object of the invention relates to a method for preparing a porous scaffold which comprises the steps consisting of:

a) preparing an alkaline aqueous solution comprising an amount of at least one polysaccharide and one cross-linking agent b) freezing the aqueous solution of step a)

c) sublimating the frozen solution of step b). characterized in that step b) is performed before the cross-linking of the polysaccharide occurs in the solution of step a).

According to the invention, the term "step b) is performed before the cross-linking of the polysaccharide occurs in the solution of step a)" means that the cross-linking of the polysaccharide occurs during the sublimation step (step c)).

In the present invention, any type of polysaccharide can be used. Synthetic or natural polysaccharides may be alternatively used for the purpose of the invention. For example, suitable natural polysaccharides include, but are not limited to dextran, agar, alginic acid, hyaluronic acid, inulin, pullulan, heparin, fucoidan, chitosan, scleroglucan, curdlan, starch, cellulose and mixtures thereof. Chemically modified polysaccharides bearing for instance acidic groups (carboxylate, sulphate, phosphate), amino groups (ethylene amine, diethylaminoethylamine, propylamine), hydrophobic groups (alkyl, benzyl) can be included. Monosaccharides that may be used to produce the desired polysaccharide include but are not limited to ribose, glucose, mannose, galactose, fructose, sorbose, sorbitol, mannitol, iditol, dulcitol and mixtures thereof. Many of these compounds are available commercially from companies such as Sigma-Aldrich (St. Louis, Mich., US).

The preferred weight-average molecular weight for the polysaccharide is from about 10,000 Daltons to about 2,000,000 Daltons, more preferably from about 10,000 Daltons to about 500,000 Daltons, most preferably from about 10,000 Daltons to about 200,000 Daltons.

In one embodiment of the invention, the polysaccharide(s) used to prepare the scaffold of the invention is a neutral polysaccharide such as dextran, agar, pullulan, inulin, scleroglucan, curdlan, starch, cellulose or a mixture thereof. In a preferred embodiment, a mixture of pullulan and dextran is used to prepare the scaffold of the invention. For example, said mixture comprises 25% of dextran and 75% of pullulan.

In another embodiment of the invention, the polysaccharide(s) used to prepare the scaffold of the invention is a positively charged polysaccharide such as chitosan, DEAE-dextran and mixtures thereof.

In another embodiment of the invention, the polysaccharide(s) used to prepare the scaffold of the invention is a negatively charged polysaccharide such as alginic acid, hyaluronic acid, heparin, fucoidan and mixtures thereof.

In another embodiment of the invention, the polysaccharide(s) used to prepare the scaffold of the invention is a mixture of neutral and negatively charged polysaccharides, wherein the negatively charged polysaccharides represents 1 to 20%, preferably 5 to 10% of the mixture.

In a particular embodiment the cross-linking agent is selected from the group consisting of trisodium trimetaphosphate (STMP), phosphorus oxychloride ($POCl_3$), epichlorohydrin, formaldehydes, water-soluble carbodiimides, glutaraldehydes or any other compound that is suitable for crosslinking a polysaccharide. In a preferred embodiment, the cross-linking agent is STMP. The concentration of the cross-linking agent in the aqueous solution (w/v) is from about 1% to about 6%, more preferably from about 2% to about 6%, most preferably from about 2% to about 3%. It is preferred to use the cross-linking agent at such an amount that the weight ratio of the polysaccharide to the cross-linking agent is in the range from 20:1 to 1:1, preferably from 15:1 to 1:1 and more preferably from 10:1 to 1:1. Many of these compounds are available commercially from companies such as Sigma-Aldrich (St. Louis, Mich., US).

The aqueous solution comprising the polysaccharide may further comprise various additives depending on the intended application. Preferably, the additive is compatible with the polysaccharide and does not interfere with the effective cross-linking of the polysaccharide(s). The amount of the additive used depends on the particular application and may be readily determined by one skilled in the art using routine experimentation.

The aqueous solution comprising the polysaccharide may optionally include at least one antimicrobial agent. Suitable antimicrobial preservatives are well known in the art. Examples of suitable antimicrobials include, but are not limited to alkyl parabens, such as methylparaben, ethylparaben, propylparaben, and butylparaben, cresol, chlorocresol, hydroquinone, sodium benzoate, potassium benzoate, triclosan and chlorhexidine. Other examples of antibacterial agents and of anti-infectious agents that may be used are, in a non-limiting manner, rifampicin, minocycline, chlorhexidine, silver ion agents and silver-based compositions.

The aqueous solution comprising the polysaccharide may also optionally include at least one colorant to enhance the visibility of the solution. Suitable colorants include dyes, pigments, and natural coloring agents. Examples of suitable colorants include, but are not limited to, alcian blue, fluorescein isothiocyanate (FITC), and FITC-dextran.

The aqueous solution comprising the polysaccharide may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

It is an essential feature of the invention that step b) is performed before the cross-linking of the polysaccharide occurs in the solution of step a) (see EXAMPLE 1). Temperature and time are the main factors to control the cross-linking of the aqueous solution. To avoid or seriously limit the cross-linking of the polysaccharide, the aqueous solution may be prepared at a temperature under 37° C., more preferably comprised between 4° C. and 25° C. Moreover, the step b) may be performed as quickly as possible to avoid the cross-linking of said polysaccharide.

Once the aqueous solution is prepared, it is frozen. The freezing of the aqueous solution may be performed at different rates (e.g., ° C./min). For example, the freezing may be performed at rate from about 1° C./min to about 200° C./min, preferably from about 1° C./min to about 20° C./min, and most preferably from about 5° C./min to about 10° C./min. The solution may be frozen in liquid nitrogen or in dried ice.

When the aqueous solution is frozen, sublimation may take place. In a preferred embodiment, the method for preparing porous scaffolds according to the present invention includes a freeze-drying process.

Therefore, according to the invention, the freeze-drying process has to take place before the cross-linking process occurs in the aqueous solution.

Freeze-drying may be performed with any apparatus known in the art. There are essentially three categories of freeze dryers: rotary evaporators, manifold freeze dryers, and tray freeze dryers. Such apparatus are well known in the art and are commercially available such as a freeze-dryer Lyovac (GT2, STERIS Rotary vane pump, BOC EDWARDS).

Basically, the deep-frozen aqueous solution is placed in a chamber. Then the chamber temperature is increased to a level higher than the boiling point of the liquefied vapour, whereby the vapour is vaporized and removed. For example, the temperature of chamber may be from −70° C. to −1° C., preferably from −70° C. to −40° C., further preferably about −50° C. to −40° C. The heating of the chamber is accompanied with a vacuum flow to decrease the pressure of the chamber. Typically the vacuum of the chamber is from 0.1 mBar to about 6.5 mBar.

The freeze-drying is performed for a sufficient time sufficient to remove at least 98.5% of the water, preferably at least 99% of the water, more preferably at least 99.5%.

The freezing of the aqueous solution causes the formation of ice particles from the water. Without to be bound by any theory, under the temperature and pressure condition described above, water included in the frozen solution is sublimed, and thus, thereby leaving interstices in the material in the spaces previously occupied by the ice particles, and accordingly formed porous scaffolds are produced. Surprisingly, the cross-linking process occurs during the freeze-drying process.

The material density and pore size of the resultant scaffold may be therefore varied by controlling the rate of freeze-drying of the frozen aqueous solution. The essential parameter in a freeze-drying process is the vacuum rate. In the examples, the inventors have indeed shown that different vacuum rates lead to different size and density of the pores in the scaffold.

The average pore size of the scaffold is from about 1 µm to about 500 µm, preferably from about 150 µm to about 350 µm, more preferably from about 175 µm to about 300 µm. The density of the pores is from about 4% to 75%, preferably from about 4% to about 50%.

In another embodiment, the method of the invention comprises a further step consisting of hydrating the scaffold as prepared according to the invention. Said hydration may be performed by submerging the scaffold in an aqueous solution (e.g., de-ionized water, water filtered via reverse osmosis, a saline solution, or an aqueous solution containing a suitable active ingredient) for an amount of time sufficient to produce a scaffold having the desired water content. For example, when a scaffold comprising the maximum water content is desired, the scaffold is submerged in the aqueous solution for an amount of time sufficient to allow the scaffold to swell to its maximum size or volume. Typically, the scaffold is submerged in the aqueous solution for at least about 1 hour, preferably for at least about 2 hours, and more preferably for about 4 hours to about 24 hours. It is understood that the amount of time necessary to hydrate the scaffold to the desired level will depend upon several factors, such as the composition of the used polysaccharides, the size (e.g., thickness) of the scaffold, and the temperature and viscosity of the aqueous solution, as well as other factors.

In a particular embodiment, the hydrated scaffold comprises 80% of water, preferably, 90% of water, most preferably 95% of water.

In another particular embodiment, the aqueous polysaccharide solution may be poured in a mould before freezing and sublimation, so that the porous scaffold obtained with the method of the invention can take a desired form. Any geometrical moulds may be used according to the invention. Different sizes may be also envisaged. For example, typically, the aqueous solution may be poured in a tubular mould with a central axis so that the porous scaffold may be tubular with a desired external and internal diameter (see EXAMPLE 6). The mould may be made of any material, but preferred material includes non sticky surfaces such as Teflon.

Alternatively, the scaffolds of the invention may be cut and shaped to take a desired size and form.

The method of the invention can further include the step of sterilizing the scaffold using any suitable process. The scaffold can be sterilized at any suitable point, but preferably is sterilized after the scaffold is hydrated. Suitable non-irradiative sterilization techniques include, but are not limited to, UV exposure, gas plasma or ethylene oxide methods known in the art. For example, the scaffold can be sterilized using a sterilisation system which is available from Abtox, Inc of Mundelein, Ill. under the trade mark PlazLyte, or in accordance with the gas plasma sterilization processes disclosed in U.S. Pat. No. 5,413,760 and U.S. Pat. No. 5,603,895.

The scaffold produced by the methods of the invention can be packaged in any suitable packaging material. Desirably, the packaging material maintains the sterility of the scaffold until the packaging material is breached.

In another embodiment, one or more biomolecules may be incorporated in the porous scaffold. The biomolecules may comprise, in other embodiments, drugs, hormones, antibiotics, antimicrobial substances, dyes, radioactive substances, fluorescent substances, anti-bacterial substances, chemicals or agents, including any combinations thereof. The substances may be used to enhance treatment effects, enhance visualization, indicate proper orientation, resist infection, promote healing, increase softness or any other desirable effect. In said embodiment, the scaffold of the invention, comprising one or more biomolecules as described here above, may be used as a controlled release system of an active agent.

In one embodiment, the biomolecule may comprise chemotactic agents, antibiotics, steroidal or non-steroidal analgesics, antiinflammatories, immunosuppressants, anti-cancer drugs, various proteins (e.g., short chain peptides, bone morphogenic proteins, glycoprotein and lipoprotein); cell attachment mediators; biologically active ligands; integrin binding sequence; ligands; various growth and/or differentiation agents (e.g., epidermal growth factor, IGF-I, IGF-II, TGF-[beta], growth and differentiation factors, stromal derived factor SDF-1; vascular endothelial growth factors, fibroblast growth factors, platelet derived growth factors, insulin derived growth factor and transforming growth factors, parathyroid hormone, parathyroid hormone related peptide, bFGF; TGF[beta] superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments, DNA plasmids, Si-RNA, transfection agents or any combination thereof.

In one embodiment growth factors include heparin binding growth factor (HBGF), transforming growth factor alpha or beta (TGF), alpha fibroblastic growth factor (FGF), epidermal growth factor (TGF), vascular endothelium growth factor (VEGF), and SDF-1, some of which are also angiogenic factors. In another embodiment factors include hormones such as insulin, glucagon, and estrogen. In some embodiments it may be desirable to incorporate factors such as nerve growth factor (NGF) or muscle morphogenic factor (MMF). In one embodiment, TNF alpha/beta, or matrix metalloproteinases (MMPs) are incorporated.

Additionally, scaffolds of the invention may optionally include anti-inflammatory agents, such as indomethacin, salicylic acid acetate, ibuprofen, sulindac, piroxicam, and naproxen; thrombogenic agents, such as thrombin, fibrinogen, homocysteine, and estramustine; and radio-opaque compounds, such as barium sulfate, gold particles and iron oxide nanoparticles (USPIOs).

Additionally, scaffolds of the invention may optionally comprise anti-thrombotic agents such as antivitamin K or aspirin, antiplatelet agents such as aspirin, thienopyridine, dipyridamole or clopidogrel (that selectively and irreversibly inhibits adenosine diphosphate (ADP)-induced platelet aggregation) or anticoagulant agent such as heparin. The combination of heparin (anticoagulant) and tirofiban (antiplatelet agent) has been shown to be effective in reducing both thrombus and thromboemboli and may be incorporated. Genistein, a potential isoflavone which possesses dose-dependent antiplatelet and antiproliferative properties and inhibits collagen-induced platelet aggregation responsible for primary thrombosis, may also be incorporated.

Methods for Using the Scaffolds of the Invention

Scaffolds of the invention are especially suited for tissue engineering, repair or regeneration. A difference in porosity may facilitate migration of different cell types to the appropriate regions of the scaffold. In another embodiment, a difference in porosity may facilitate development of appropriate cell-to-cell connections among the cell types comprising the scaffold, required for appropriate structuring of the developing/repairing/regenerating tissue. For example, cell processes extension may be accommodated more appropriately via the varied porosity of the scaffolding material. Therefore, the scaffold may comprise cells of any tissue.

In particular embodiment, the cells are seeded on said scaffold. In another embodiment, the scaffolds of the invention are submerged in a culture solution comprising the desired cells for an amount of time sufficient to enable penetration of the cells throughout the scaffold.

In another embodiment, scaffold of the invention is capable of supporting the viability and the growth of seeded cells in culture over long periods of time without inducing differentiation.

In another embodiment, scaffold of the invention provides an environment for unstimulated cell growth (without activation by growth stimulants)

In another embodiment, scaffold of the invention can be used to study physiological and pathological processes such as tissue growth, bone remodeling, wound healing, tumorigenesis (including migration and invasion), and angiogenesis. Scaffold allows the creation of defined and controlled environments where specific processes can be modulated and studied in a controlled manner free of endogenous factors.

In particular, scaffold of the invention can be used for 3D culture for diagnostic or toxicological dosages. In this embodiment, the scaffold of the invention would allow evaluation of the toxicity of a product directly on cells present in a 3D environment. In said embodiment, the scaffold of the invention is used for cultivating cells useful for the evaluation of the toxicity and/or pharmacology of a product, such as hepatocytes, embryonic stem cells, epithelial cells, keratinocytes, or induced pluripotent stem cells (iPS cells).

In another embodiment, scaffold of the invention is capable of supporting growth and differentiation of cell types in vitro and in vivo.

In another embodiment, the cells are stem or progenitor cells. In another embodiment the cells may include but are not limited to chondrocytes; fibrochondrocytes; osteocytes; osteoblasts; osteoclasts; synoviocytes; bone marrow cells; mesenchymal cells; epithelial cells, hepatocytes, muscle cells; stromal cells; stem cells; embryonic stem cells; precursor cells derived from adipose tissue; peripheral blood progenitor cells; stem cells isolated from adult tissue; induced pluripotent stem cells (iPS cells); genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of progenitor cells isolated from adult tissue and other cells; a combination of peripheral blood progenitor cells and other cells; a combination of stem cells isolated from adult tissue and other cells; and a combination of genetically transformed cells and other cells.

In another embodiment, any of these cells for use in the scaffolds and methods of the invention, may be genetically engineered to express a desired molecule, such as for example heparin binding growth factor (HBGF), transforming growth factor alpha or beta (TGF.beta.), alpha fibroblastic growth factor (FGF), epidermal growth factor (TGF), vascular endothelium growth factor (VEGF) and SDF-1, some of which are also angiogenic factors. In another embodiment expressed factors include hormones such as insulin, glucagon, and estrogen. In another embodiment factors such as nerve growth factor (NGF) or muscle morphogenic factor (MMF), or in another embodiment, TNF alpha/beta are expressed.

In a particular embodiment, scaffolds of the invention are suitable to prepare vascular substitutes to replace compromised arteries as described for example, in Chaouat et al. (Chaouat M, Le Visage C, Autissier A, Chaubet F, Letourneur D. The evaluation of a small-diameter polysaccharide-based arterial graft in rats. Biomaterials. 2006 November; 27(32): 5546-53. Epub 2006 Jul. 20). Such substitutes may be prepared according to the methods of the invention by using a mould as above described. Such substitutes may then comprise a population of cells to reconstruct in vitro or in vivo a vessel. In another embodiment the cells may include but are not limited to Mesenchymal Stem Cells (MSC), Endothelial Progenitor cells (EPCs), endothelial cells, fibroblastic cells and smooth muscle cells.

In another particular embodiment, scaffolds of the invention are suitable to prepare cartilage or bone implants. In such a way, the scaffolds of the invention may be loaded with chondrocytes, osteocytes; osteoblasts; osteoclasts; vascular cells or mixtures thereof, and may be cultured in presence of differentiating agents.

The site of implantation is dependent on the diseased/injured tissue that requires treatment. For example, to treat structural defects in articular cartilage, meniscus, and bone, the cell-seeded composite scaffold will be placed at the defect site to promote repair of the damaged tissue.

In case of central nervous system (CNS) injuries, the composite scaffold can be seeded with a combination of adult neuronal stem cells, embryonic stem cells, glial cells and Sertoli cells. In the preferred embodiment, the composite scaffold can be seeded with Sertoli cells derived from transformed cell lines, xenogeneic or allogeneic sources in combination with neuronal stem cells. The Sertoli cells can be cultured with the composite scaffold for a period before addition of stem cells and subsequent implantation at the site of injury. This approach can circumvent one of the major hurdles of cell therapy for CNS applications, namely the survival of the stem cells following transplantation. A composite scaffold that entraps a large number of Sertoli cells can provide an environment that is more amenable for the survival of stem cells.

Accordingly, the porous polymer scaffold, which is prepared according to the present invention, can be effectively used as a raw material for fabricating artificial tissues or organs such as artificial blood vessels, artificial esophagus, artificial bladder, artificial nerves, artificial hearts, prostatic heart valves, artificial skins, orthopedic implants, artificial muscles, artificial ligaments, artificial respiratory organs, etc. Further, the porous polymer scaffold of the present invention can be prepared in the form of a hybrid tissue by blending or incorporating on or into other types of biomaterials and with functional cells derived from tissues or organs. It may have various biomedical applications, for example, to maintain cell functions, tissue regeneration, etc.

Alternatively scaffolds of the invention may be used for cell delivery for therapeutic use. Actually, scaffolds of the invention may be used as a raw material for preparing cell delivery systems that can be administered to a subject for therapeutic or diagnostic purposes. In a particular embodiment, scaffolds of the invention may be used to prepare a patch, a biofilm or a dressing that can be loaded with cells, preferentially with autologous cells. Human and animal cells can be obtained after cell culture and directly from frozen stocks of cells. For example, scaffolds of the invention may used to prepare a dressing containing cells that can be applied on the skin, for reconstructing or healing the skin. Alternatively, said dressing may used to be applied on the heart of a subject for treating ischemia (myocardial infarction). In those embodiments, the cells that are entrapped in the scaffold can thus migrate into the targeted tissue or organ.

In another embodiment, scaffolds of the invention may be used for culturing cells. Cells may then be stimulated to undergo growth of differentiation or other physiological processes by the addition of appropriate growth factors. Culture medium containing one or more cytokines, growth factors, hormones or a combination thereof, may be used for maintaining cells in an undifferentiated state, or for differentiating cells into a particular pathway.

More particularly, the scaffold of the invention may be used for producing molecules of interest. Actually, scaffolds of the invention may be used to provide a biological environment for the anchorage of cells in a bioreactor, so that the cells can produced the desired molecules. The scaffolds of the invention provide mechanical and biochemical protection of the cultured cells.

The scaffolds may thus serve as a cell reservoir for producing desired molecules such as proteins, organic molecules, and nucleotides. For example, proteins of interest include but are not limited to growth factors, hormones, signal molecules, inhibitors of cell growth, and antibodies. Scaffolds of the invention are particularly interesting for producing monoclonal antibodies. Scaffolds of the invention may be also suitable to produce organic molecules such as flavours, therapeutic molecules.

In this purpose, the scaffolds of the invention may be loaded with any type of cells, including prokaryotic and eukaryotic cells. For examples, scaffolds of the invention may be load with bacteria, yeast cells, mammalian cells, insect cells, plant cells, etc. Specific examples include *E. coli*, *Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). More particularly, the invention contemplates the use of established cell lines such as hybridomas. Alternatively, the cells may be genetically engineered to express a desired molecule as described above.

The scaffold of the invention may be loaded with cells, cultured for a certain period of time then the cells can be retrived/extracted/separated from the scaffold for further use, such as therapeutic or diagnostic applications or cell analysis. Separation of the cells from the scaffold may involve the use of enzymes that could degrade the scaffold, such as pullulanase and/or the use of enzymes that could detach the cells such as collagenase, elastase or trypsin or cell-detaching solutions such as EDTA.

The invention will further be illustrated in view of the following figures and examples.

FIGURES

FIG. 1: Macroscopic appearance of a circular porous scaffold after rehydration

Figure 2:
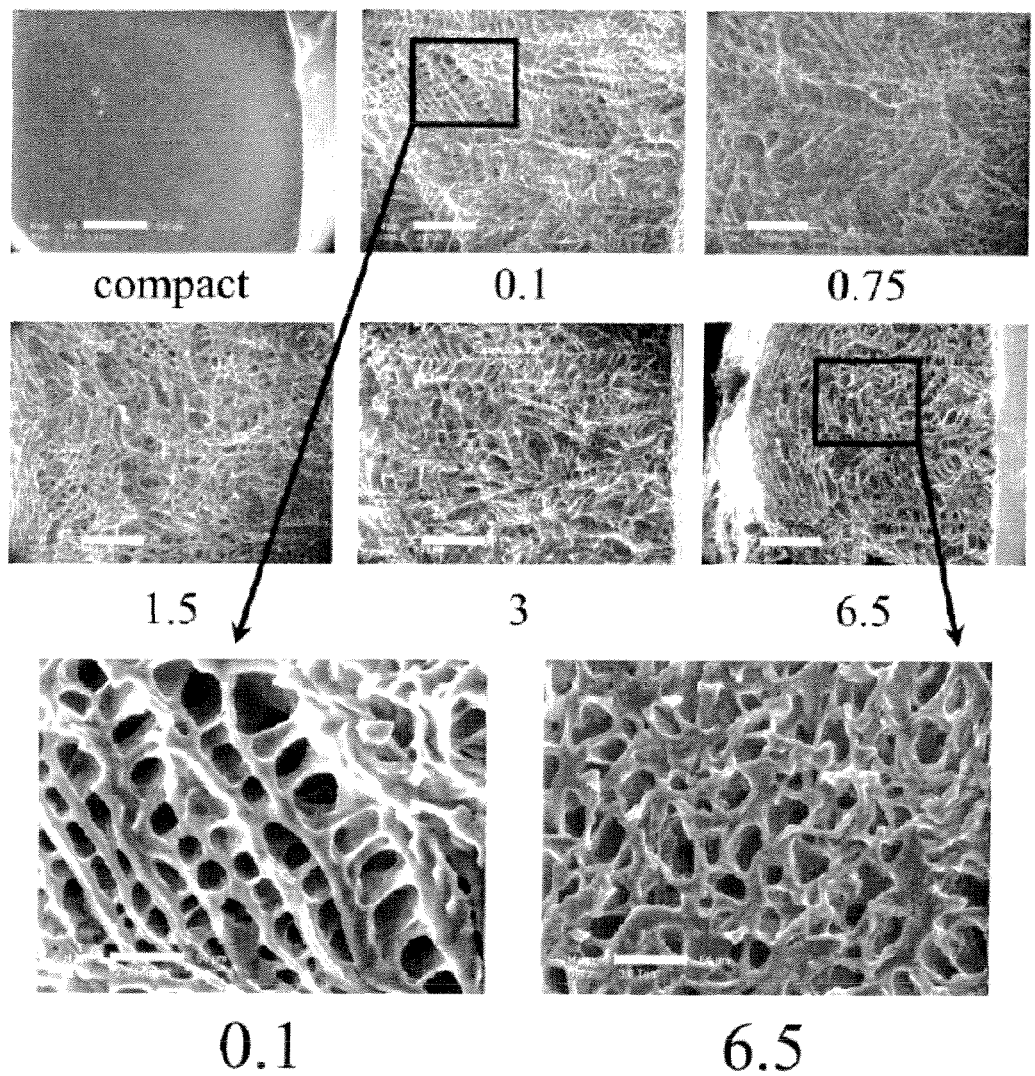

FIG. 2: Microscopic observation by ESEM of porous hydrated scaffolds as a function of the freeze-drying process conditions (vacuum in mbars). Scale bar: 200 microns, except for the high magnification (50 microns).

Figure 3:
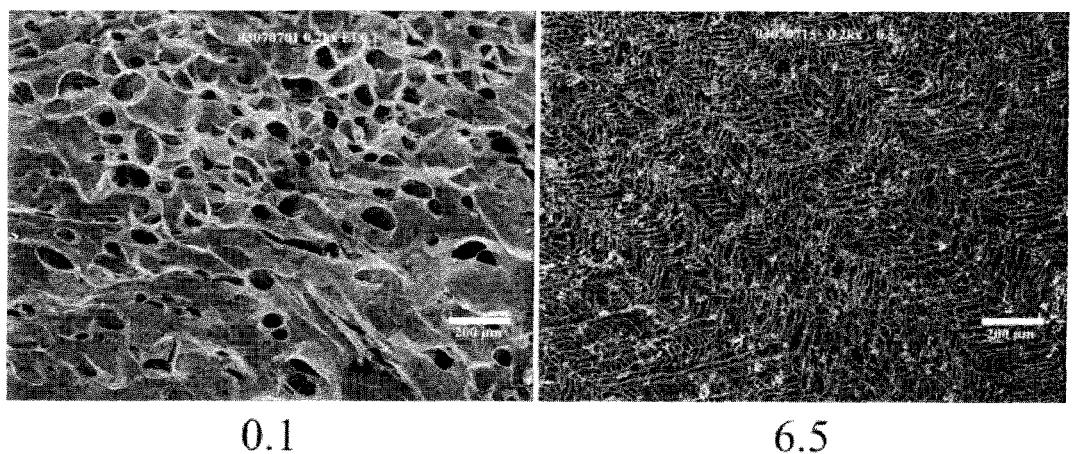

FIG. 3: SEM observation of porous dried scaffolds prepared at either 0.1 mbar (left) or 6.5 mbar (right).

Figure 4:
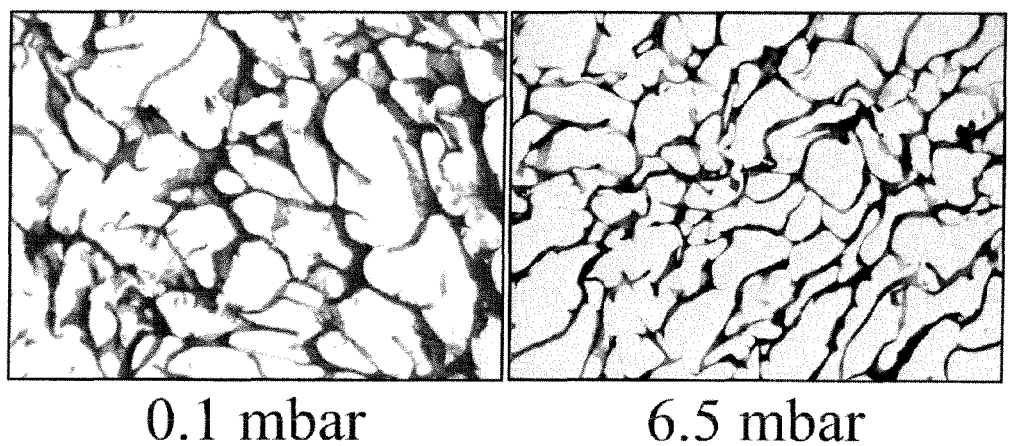

FIG. 4: Observation of H&E staining of porous scaffold sections prepared at either 0.1 mbar or 6.5 mbar (magnification, ×40).

Figure 5:
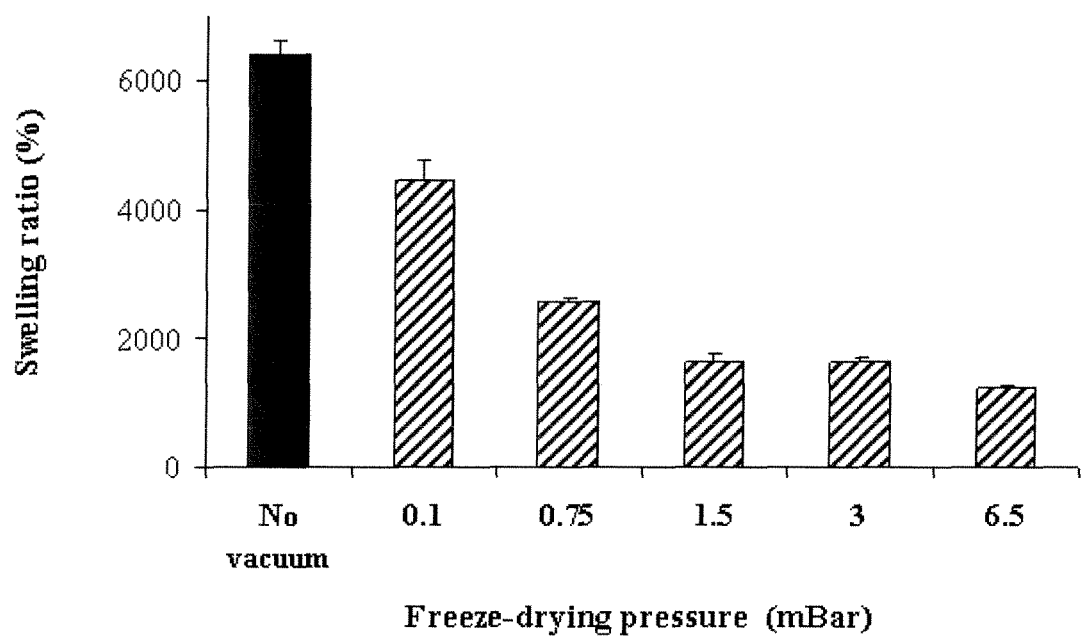

FIG. 5: Swelling ratio as a function of the freeze-drying pressure.

Figure 6:
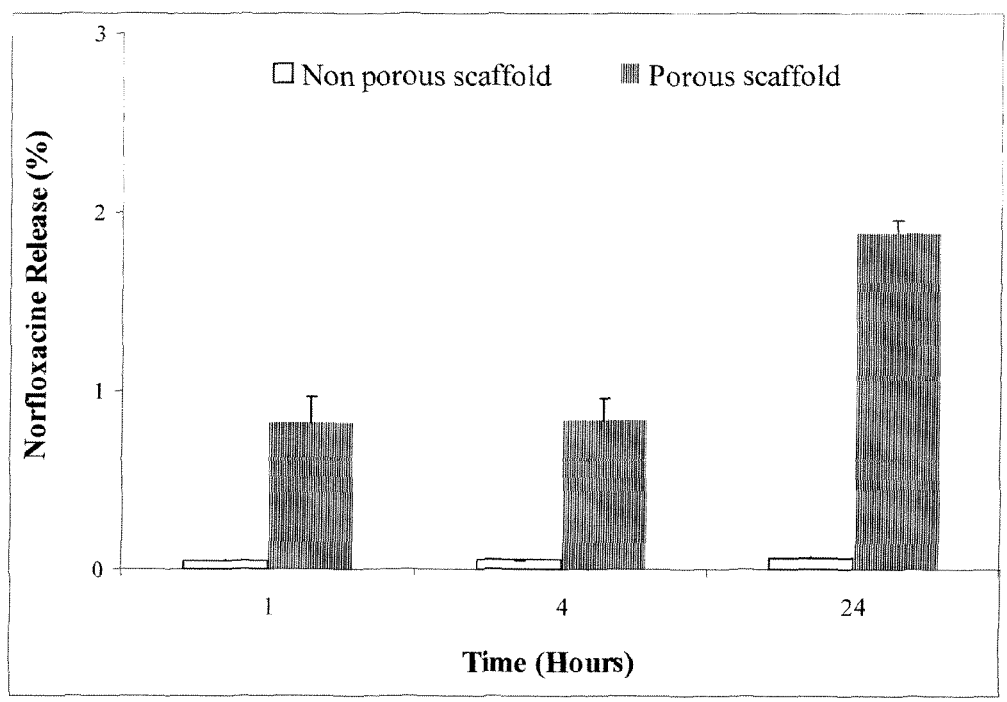

FIG. 6: Release of norfloxacin from porous scaffold, as compared to release from non-porous scaffolds prepared in the absence of porogen agent.

EXAMPLES

Example 1

Polysaccharides-Based Scaffolds Preparation

A mixture of pullulan/dextran 75:25 with a total concentration in water of 24.5% (w/v) (pullulan, MW 200,000, Hayashibara Inc., Okayama, Japan; dextran MW 500,000, Pharmacia) was prepared. Chemical cross-linking of polysaccharides was carried out using the cross-linking agent sodium trimetaphosphate (STMP) (11% (w/v), Sigma) under alkaline conditions. Briefly, 9 mL of the polysaccharide solution was mixed with 1 mL of NaOH 10M and 300 mg of STMP in 1 mL of water were then added to the mixture. The solution was immediately poured into a 60 mm Petri dish then stored at −80° C. Cross-linking was performed on the frozen mixture during a freeze-drying process in Lyovac freeze-dryer (GT2, STERIS Rotary vane pump, BOC EDWARDS). Scaffolds were freeze-dried for 24 h to allow the complete removal of water. Scaffolds cross-linked during the freeze-drying process were opaque and slightly brittle. They could easily be cut at the desired size and shape and could be rehydrated (FIG. 1).

A control experiment was performed by freeze-drying scaffolds obtained after chemical crosslink carried out at 50° C. However, these dried scaffolds could not be rehydrated properly since their overall structure was damaged after the freeze-drying process. Another experiment was performed by omitting the cross-linking agent in the process. In this condition, the freeze-drying protocol only leads to a solution and not to a scaffold.

Example 2

Influence of the Freeze-Drying Conditions

Preparation of polysaccharide scaffolds was conducted according to example 1. For the freeze-drying step, different vacuums were adjusted (0.1 mbar, 0.75 mbar, 3 mbar, 1.5 mbar, and 6.5 mbar) using a controlled leak.

Resulting scaffolds were characterized using Environmental Scanning Electron Microscopy (ESEM) and Scanning Electron Microscopy (SEM). The surface of scaffolds in their hydrated state was directly observed using an ESEM-FEG (Philips XL 30, Netherlands with an accelerating voltage of 15 kV at a pressure of 4 torr), since ESEM technique does not require any dehydration of the samples. ESEM images of the scaffolds in their swollen state indicated that these scaffolds were porous (FIG. 2). Scaffolds lyophilized at 0.1 mbar (high vacuum) presented pores with larger diameters than those prepared at 6.5 mbar (low vacuum). For low vacuum conditions, the network of the scaffolds was better organized, homogeneous with interconnected pores throughout the scaffold. SEM images of the dried scaffolds confirmed that the scaffolds cross-linked during the freeze-drying process were porous (FIG. 3). For histological staining, scaffolds were fixed in 4% paraformaldehyde/PBS, then they were OCT-embedded (Tissue Teck-OCT (EMS, Washington, Pa.) and frozen in liquid nitrogen cooled-isopentane. The frozen samples were cryosectioned (10 μm sections) using a cryostat (Leica CM 1900). Hematoxylin/eosin staining was performed on scaffold sections to visualize the structure of the scaffolds.

The appearance of the scaffolds on histological sections was consistent with electronic microscopy images (FIG. 4). The inner porous structure of the scaffolds could be modulated by varying the freeze-drying vacuum. Scaffolds cross-linked at low vacuum (6.5 mbar) presented a structure with small pores compared to the scaffolds cross-linked at high vacuum (0.1 mbar) that presented a loose network.

Example 3

Swelling Ratio

Preparation of polysaccharide scaffolds was conducted according to example 2. Freeze-dried scaffolds were cut with a razor blade to obtain rectangular-shaped scaffolds (2.5 cm×2 cm, thickness: 3 mm). Scaffolds were washed in deionized water to remove all buffer salts, then dehydrated at 50° C. for 36 hours. The weight of the samples in their dry (W dry) and swollen (W swollen) states after rehydration in deionized water for 24 hours were measured using an electronic balance (AG 204 Deltarange® mettler Toledo; max 81 g/210 g; d=0.1 mg/1 mg). Before weighting, the swollen scaffolds were carefully laid on a soft paper to remove the excess of water. Each experiment was performed in triplicate. The swelling ratio was calculated according to the formula:

$$\text{Swelling ratio} = ((W\text{wollen} - W\text{dry})/W\text{dry}) \times 100.$$

The swelling ratio of porous scaffolds increase with an increase of the freeze-drying vacuum (FIG. 5). The lowest swelling ratio was found for the scaffolds prepared at the lowest vacuum (6.5 mbar).

Example 4

Cellular Infiltration

Femoral bone marrow Mesenchymal Stem Cells (MSC) from Wistar rat were cultured on scaffolds prepared as in Example 1. A circular punch was used to cut 6 mm diameter and 1 mm thickness round-shaped porous scaffolds. Before cell seeding, scaffolds were allowed to equilibrate in culture medium in 24-well plates at 37° C. for 24 hours. Culture medium consisted of low glucose DMEM (Gibco, Life Technology, New York) with 10% fetal bovine serum and 1% penicillin/streptomycin (Sigma). Cells were seeded on top of the scaffolds (cell density $10^6$ cells/scaffold). Culture medium, supplemented with ascorbic acid (50 μg/ml) was changed every 2-3 days. Samples were maintained in culture for up to 1 week. Non-seeded porous scaffolds incubated in culture medium were used as controls. Similar experiments were successfully carried out with other cell types such as primary vascular smooth muscle cells and endothelial cells from animal and human origin.

Initial attachment: Cells attached in less than 2 hours on porous scaffolds surfaces, with MSCs infiltrating the scaffolds.

Cell tracking: Cell tracking was performed by labeling the cells prior to the seeding step with a fluorescent dye PKH26 (Sigma) according to the manufacturer's instructions. Cells were seeded on both unlabeled and FITC-scaffolds. The seeded scaffolds were then fixed in 4% paraformaldehyde/PBS before analysis by confocal microscopy (Zeiss LSM 510).

PKH26 labeled-MSCs were tracked throughout the pores of the scaffold. Representative images of the cellular distribution within the gels were taken at the depth of 70 and 190 microns for day 1 and day 7. A z-axis projection of the confocal images confirmed the cellular infiltration within the gel. We noticed from day 1 to day 7 an increase of the cellular density within the scaffolds.

Cell viability: Cell viability was assayed using Calcein AM (Calbiochem, San Diego Calif.) which is a polyanionic dye hydrolyzed by live cells thus producing an intense uniform green fluorescence (wavelength 485-535 nm). This dye was added according to the manufacturer's instructions to porous unlabeled and FITC-scaffolds at day 1, day 5 and day 7. The seeded scaffolds were then fixed in 4% paraformaldehyde/PBS before analysis by confocal microscopy (Zeiss LSM 510) to visualize cell distribution within the scaffolds and FITC-scaffolds.

With this assay, we confirmed that most of the cells were alive at day 1 and day 7 on the surface of and inside porous scaffolds.

Example 5

Protein Incorporation into the Scaffolds

Preparation of polysaccharide scaffolds was conducted according to example 1 with the following modifications to incorporate adhesion proteins such as gelatin and collagen type I. For gelatin, 9 mL of polysaccharide solution was mixed with 1 mL of NaOH 10M then 300 mg of STMP in 1 mL of water containing 500 μg of gelatin (500 μL of a 0.1% gelatin solution) were added to the mixture. Incorporation of collagen type I was performed by adding 500 μL of a 0.4% collagen solution (Upstate #08115) into the polysaccharide solution before adding the cross-linking reagent (300 mg in 500 μL Coomassie Blue and Sirius Red staining on thick sections of the scaffolds confirmed the protein distribution within the scaffold. Average protein content was estimated to be about 1 μg of gelatin per 6 mm diameter scaffold, and 4 μg of collagen per 6 mm diameter scaffold.

Example 6

Tubular Scaffold as Vascular Substitutes

Polysaccharides-based tubular scaffolds prepared as described in example 1 could be used as vascular substitute.

An aqueous solution prepared as described as in example 1 was poured in a home made tubular mould consisting of a 20G needle and the needle's cap. The needle (20G×1$^{1/2}$" or 0.9×40 mm) was used as a central axis to create a smooth surface of the lumen (2 mm lumen diameter). The polysaccharide/STMP solution was injected into the needle through the needle's cap using a 1 ml syringe. Both internal and external diameters of the resulting tubular scaffold depend on the size of the needle and its cap (samples were also prepared using 18G or 21G needles).

According to example 1, the mould was immediately frozen at −80° C. Secondarily the mixture was freeze-dried as described above. After freeze-drying, the scaffolds were easily removed from the mould. After rehydration in PBS, tubular-shaped scaffolds were obtained. Cells such as smooth muscle cells or mesenchymal stem cells can be seeded into the tubular scaffold during the rehydration process and then other cells such as endothelial cells or endothelial progenitor cells can be loaded into the lumen of the tubular scaffold.

Example 7

Drug Incorporation into the Scaffolds

Preparation of polysaccharide scaffolds was conducted according to example 1 with the following modifications to incorporate drugs such as norfloxacin. Norfloxacin, a fluoroquinolone carboxylic acid, is a widely used antimicrobial agent. It currently regarded as model compound of low bioavailability, mainly attributed to its low aqueous solubility. Norfloxacin (Sigma) was added in the solid state (60 mg) to the polysaccharides solution (10 g) and the mixture stirred until homogeneity was attained. The resulting mixture was then mixed with 1 mL of NaOH 10M then 300 mg of STMP in 1 mL of water were added to the mixture. Cross-linking process was then conducted according to example 1.

Release profiles were obtained by incubating porous scaffolds in PBS at 37° C. for up to 24 hours. Norfloxacin content in supernatants was assayed spectrophotometrically at 274 nm. FIG. 6 illustrates the release of norfloxacin from porous scaffold, as compared to release from non-porous scaffolds prepared in the absence of porogen agent.

The invention claimed is:

1. A method for preparing a porous scaffold consisting of the steps of
   a) preparing an alkaline aqueous solution consisting of an amount of at least one natural polysaccharide and one cross-linking agent;
   b) freezing the aqueous solution of step a); and
   c) sublimating the frozen solution of step b);
   wherein the at least one natural polysaccharide is selected from the group consisting of dextran, agar, alginic acid, hyaluronic acid, inulin, pullulan, heparin, chitonsan, and fucoidan; and
   wherein step b) is performed before the cross-linking of the natural polysaccharide and said cross-linking occurs during the sublimation step c).

2. The method according to claim 1 wherein said cross-linking agent is selected in the group consisting of trisodium trimetaphosphate (STMP), phosphorus oxychloride (POCl3), eupichlorohydrin, formaldehydes, water soluble carbodiimides, and glutaraldehydes.

3. The method according to claim 2 wherein said cross-linking agent is trisodium trimetaphosphate (STMP).

4. The method according to claim 1 wherein the aqueous solution of step a) is freeze-dried.

5. The method according to claim 4 wherein the aqueous solution of step a) is freeze-dried under a pressure from 0.1 mBar to 6.5 mBar.

6. The method according to claim 1 wherein the aqueous solution of step a) is poured in a mould before step b).

7. The method according to claim 1 wherein said scaffold is shaped.

* * * * *